United States Patent [19]

Pedergrass et al.

[11] 4,180,869

[45] Jan. 1, 1980

[54] STOCKINGS

[75] Inventors: John E. Pedergrass, Seneca, S.C.; Cynthia A. Wichman, St. Charles, Ill.

[73] Assignee: Colgate-Palmolive Company, New York, N.Y.

[21] Appl. No.: 812,057

[22] Filed: Jul. 1, 1977

[51] Int. Cl.² .................... A61F 13/08; A41B 11/04
[52] U.S. Cl. ........................................ 2/240; 128/165
[58] Field of Search ................. 2/240, 239, 241, 409; 66/177; 128/165

[56] References Cited

U.S. PATENT DOCUMENTS

| 236,509 | 1/1881 | Ordway | 2/407 |
| 1,287,870 | 12/1918 | Burk | 2/240 X |
| 3,362,029 | 1/1968 | Comera | 66/177 X |

Primary Examiner—H. Hampton Hunter

[57] ABSTRACT

In a full length therapeutic stocking of the type having a boot portion including elastomeric yarn, waist support means spaced above the boot portion, and a hip panel extending between the boot portion and the waist support means, that improvement including a pair of stocking supports extending between and attached to the waist support means and the boot portion, each support comprising a strip of fabric extending from a respective point at the waist support means to a respective point at the upper edge of the boot portion, and each of the respective points of one of the supports being spaced circumferentially of the stocking from the corresponding respective point of the other of the supports.

10 Claims, 3 Drawing Figures

FIG I

STOCKINGS

This invention is related to therapeutic stockings and, more particularly, to so-called full leg length therapeutic stockings.

Therapeutic stockings including elastomeric-containing yarns which exert a compressive pressure on the covered portion of the leg are well-known, and have been constructed in a variety of lengths and styles. The degree of compression exerted similarly has been varied over a relatively large range. In general, however, it is understood that the pressure profile of a properly fitted stocking should gradually decrease from the patient's ankles to the upper thighs.

Three principal types of such therapeutic stockings are the so-called knee length stockings, thigh length stockings, and full length or panty style stockings. A typical thigh length stocking is shown in U.S. Pat. No. 3,728,875, issued to The Kendall Company as the assignee of Hartigan et al. on Apr. 24, 1973. A typical full length stocking, of a type sold by The Kendall Company, assignee of the present application, is disclosed in pending application Ser. No. 593,159 entitled "Therapeutic Stocking", filed July 3, 1975 in the names of Roger T. Swallow and John E. Pendergrass and assigned to The Kendall Company now U.S. Pat. No. 4,027,667, issued June 7, 1977. Both said patent and said application are hereby incorporated herein by reference.

Knee and thigh length stockings are typically held in place on the wearer by an at least partially leg-encircling garter band of elastic material, typically including an inner surface of a non-slip material such as urethane elastomer. One problem with such stockings is that the elastic band is often quite stiff and must bear against the leg with some pressure if it is satisfactorily to hold the stocking in place. This pressure, especially in some thigh length stockings, may undesirably constrict the plexus deep and superficial blood vessels. A second drawback to knee and thigh length stockings is that it is difficult to keep them in place on an active or ambulatory patient. Additionally, some thigh length stockings may roll, causing undesirable restriction and reducing protection of the leg.

Full length stockings avoid some of these problems. Rather than using a leg-encircling garter, full length stockings are supported by a pair of panels, each extending from the upper thigh over the outer hip to a waist band. This manner of support greatly reduces slippage, and reduces also many of the problems of undesirable pressure and constriction.

There are, however, problems that remain. Some patients, particularly those with large flaccid inner thighs, find that the side hip panels pull the edge of the stocking against the skin in the inside of the thigh, causing irritation, that the inner edge is pulled uncomfortably up into the groin, and that the inner edge rolls thereby acerbating the irritation and discomfort.

Accordingly, it is a primary object of the present invention to provide an improved system for supporting a full length stocking that reduces irritation, discomfort and edge rolling without adversely affecting the pressure profile. Other objects include providing such a support system which makes possible better control of the stocking's pressure profile on the upper leg.

The invention features, in a full length therapeutic stocking of the type having a boot portion including elastomeric yarn, waist support means spaced above the boot portion, and a hip panel extending between the boot portion and the waist support means, that improvement including a pair of stocking supports extending between and attached to the waist support means and the boot portion, each support comprising a strip of fabric extending from a respective point at the waist support means to a respective point at the upper edge of the boot portion, and each of the respective points of one of the supports being spaced circumferentially of the stocking from the corresponding respective point of the other of the supports. In preferred embodiments in which each support is an inelastic strip overlying and stitched to a respective inner edge of the hip panel, the distance between the respective points at the top edge of the boot portion is in the range of 20 to 40 percent of the total circumference of the top edge. In other embodiments, an insert of circumferentially elastic material, preferably doubled with the fold line at the top edge, is provided intermediate the respective points at the top edge of the boot portion and extending downwardly from the top edge.

Other objects, features and advantages will appear from the following detailed description of embodiments of the invention, taken together with the attached drawings in which.

Figure 1:
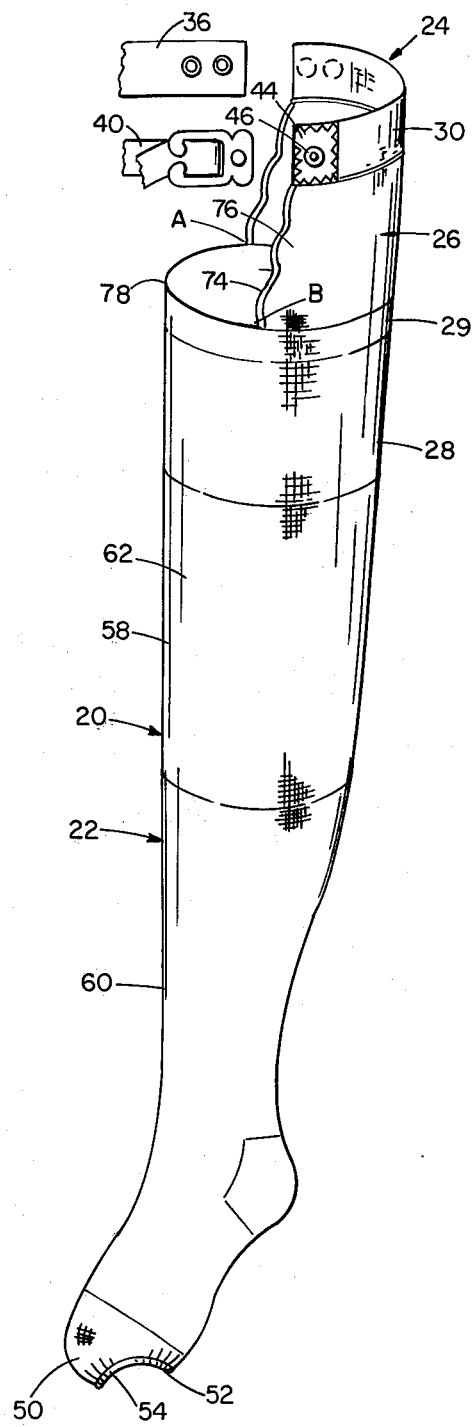
FIG. 1 is a plan view of a stocking embodying the invention.
Figure 2:
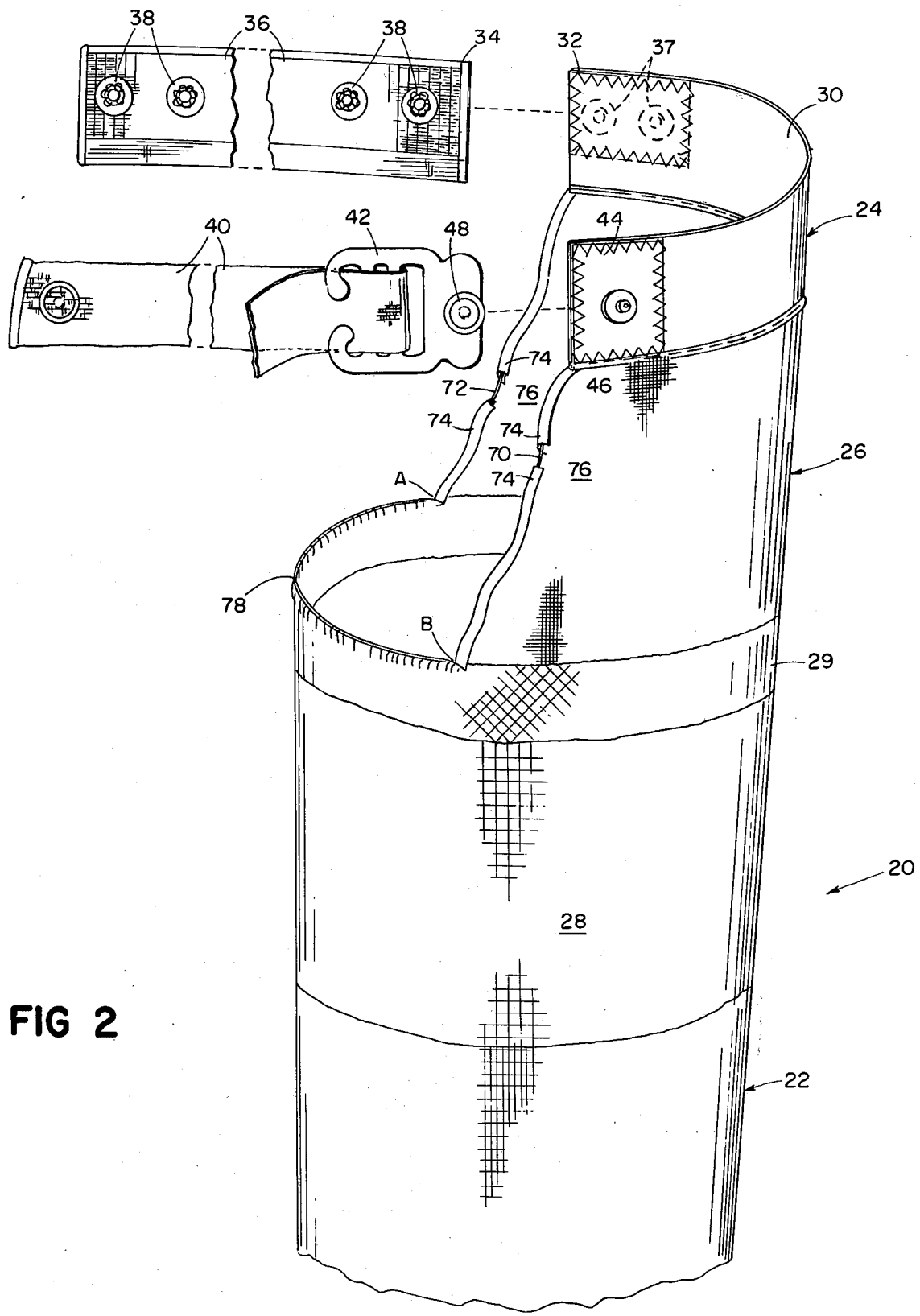
FIG. 2 is a perspective view of portions of the stocking of FIG. 1.

Referring now to FIGS. 1-2, there is shown a therapeutic stocking generally designated 20 having a boot portion 22, a waist support means 24, and a hip panel 26 extending between the waist support means 24 and the boot portion 22. The boot portion 22 exerts a compressive pressure against the patient's leg to increase the velocity of blood flow in the leg, and reduces incidence of thromboembolism in the patient. In a preferred form, the pressure profile defined by the stocking gradually decreases from the patient's ankle to the upper thigh although compressive pressure may be reduced somewhat in the area of the knee. The stocking boot portion 22 has an upper thigh panel 28 for exerting a predetermined compressive pressure against the upper thigh of the patient's leg. The stocking 20 also has a run resistant section or area 29 which preferably extends circumferentially around the stocking and is located intermediate the upper thigh panel 28 and hip panel 26.

The support means 24 has an elastic band 30 secured by suitable means, such as an overedge stitch, to the upper end of the hip panel 26. As shown, the band 30 is arranged to extend from the front around the hip to the back of the patient. The back end 32 of the band 30 is releasably attached to one end 34 of an elastic connecting band 36, which is in turn connected to the back of the other stocking (not shown) worn by the patient, by a pair of male and female snap fasteners 37 and 38, respectively. The front end 44 of band 30 is attached to an elastic or inelastic front band 40, as desired, which may have a smaller width than the side band 30. The opposed ends of the front band 40 are slidably received in a pair of fastening elements 42 to permit adjustment of the band 40, and are releasably attached by the fastening elements 42 to the front end 44 to stockings worn by the patient by male and female snap fasteners 46 and 48.

The foot portion 50 of stocking 20 has an edging 52, such as welt, which defines a toe inspection opening 54 which overlies the toes when the stocking is worn. Accordingly, an outer toe portion of the stocking may be pulled over the toes to inspect the toes through the opening 54 without removal of the stocking from the patient.

Referring to FIG. 1, the stocking 20 may be formed as follows. The lower boot portion 58 is made of a circumferentially elastic fabric having a limited vertical stretch, and has a calf panel 60, and a knee panel 62 which extends between the calf panel 60 and the upper thigh panel 28, with the calf panel 60 exerting a greater compressive pressure against the wearer's leg than the knee panel 62. A lower thigh panel may be included in between the knee panel and the upper thigh panel, if desired. The panel 62, as well as the panel 60, are of alternating courses of jersey knit stitches of non-elastomeric yarns of stretch nylon. The upper thigh panel 28 preferably has contiguous courses of jersey knit stitches of non-elastomeric yarns. A covered elastomeric yarn is inlaid into the courses as desired.

The hip panel 26 is preferably made of a two-way stretch fabric, and have alternating courses of jersey knit stitches of a covered elastomeric yarn. The section 29 of run resistant fabric has courses of stitches of a covered elastomeric yarn. Alternate rounds of the yarns have jersey knit stitches, and alternate rounds are separated by non-elastomeric yarns in different courses, with the section 29 having a two-way stretch.

The particular yarns, knit stitches and the like employed in boot portion 22 and hip panel 26 may be varied, as known to those in the field. The preferable construction is discussed in some detail in said application Ser. No. 593,159, already incorporated by reference.

After the stocking blanks have been knitted and boarded, the blanks are cut, according to the present invention, to define the front and back inner side edges 70, 72, respectively of the hip panel 26, and the intermediate top edge 78 of run resistant section 29. Rear inner side edge 72 extends from the upper edge of the hip panel adjacent end 32 of waistband 30 to a point A on top edge 78 at the rear portion of run resistant section 29; front inner side edge 72 from adjacent end 44 of waistband 30 to a point B on top edge 78 at the front of run resistant section 29. The distance (circumferentially of run resistant section 29 in a clockwise direction as shown in FIG. 2) from point B to point A is in the range of 20% to 40%, preferably about one-third, of the total circumference of run resistant section 29; and the points are spaced equidistantly from the middle of hip panel 26. Top edge 78 is sewn or stitched as required to prevent unraveling.

An inelastic edging 74 is attached along each of the inner side edges 70, 72 of the hip panels 26 to provide support for stocking 20, particularly in the area between points A and B which is not directly supported by hip panel 26. Edging 74 also provides a comfortable inner side edge of the hip panel, prevents elastomers in the hip panel from pulling out of the edging 74, and minimizes the formation of runs in the hip panel. The edging 74 may be of any suitable type, such as a Mauser stitch or edging, known to the art as stitch type 607, as defined by Federal Standard No. 751a, Jan. 25, 1965, entitled "Stitches, Seams, and Stitching". The hip panel 26 is pre-stretched along its inner side edges 70, 72 before the edging 74 is formed along the side edges. After the formation of the edging 74 on the pre-stretched fabric, the sides of the hip panel 26 are released and the edgings from a puckered configuration of the hip panel along the edgings, and a slightly arcuate inner edge of the hip panel. Although the edging 74 itself is inelastic and is not permitted to expand, the side margins 76 of the hip panel 26 along the edging 74 is permitted to expand somewhat during use of the stocking, since the edging 74 was attached with the side margins of the hip panel being pre-stretched.

When the stocking 20 is placed on a patient, the lower boot portion 58 and hip panel 26 are adjusted to position points A and B on the inside of the patient's upper leg, on opposite sides of the middle of the groin. In this position, the strips of edging 74 support the stocking in place without pulling the stocking edge between points A and B uncomfortably into the groin or adversely affecting the desired pressure profile.

Figure 3:
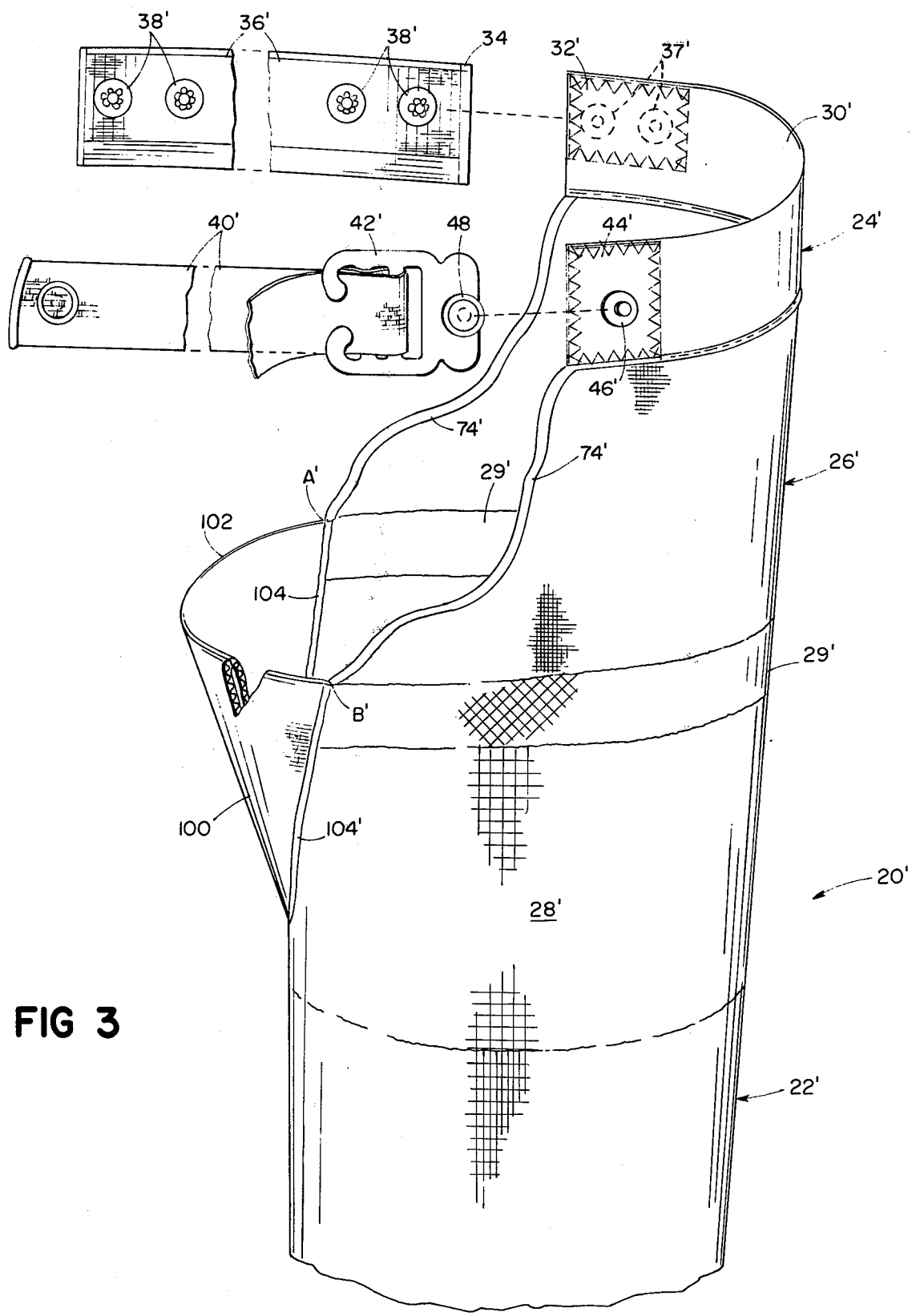
FIG. 3 is a perspective view of portions of a second embodiment of the invention.

Reference is now made to FIG. 3 which illustrates a stocking 20' embodying the invention and especially suitable for use on patients with large upper thighs. Most portions of stocking 20' are substantially identical to corresponding portions of previously described stocking 20, and are identified by the same reference numerals as those used in the foregoing description of stocking 20, with a differentiating prime (') added. As shown, an insert 100 in the form of a rounded "V" has been inserted in upper thigh panel 28' between points A' and B'. The insert 100 is symmetrical about a line midway between points A and B, the top 102 of the insert 100 forms a continuous line with the upper edge of run resistant section 29', and the edges of insert 100 are attached to the upper thigh portion 28' by overedge stitching 104.

In the FIG. 3 embodiment, stocking 20' was initially knitted, boarded, and cut with run resistant section 29' forming a continuous loop and points A' and B' coincident. The run resistant section 29' and upper thigh portion were then slit to provide the space for insert 100. As shown, the top 102 of insert 100 has a length equal to about 30% that of run resistant section 29. Thus, as will be seen from comparison of FIGS. 2 and 3, the insert 100 flares outwardly as compared to the corresponding portion of stocking 20, and stocking 20' provides a superior fit on patients with large or flaccid upper, especially inner, thighs.

Preferably, insert 100 is of doubled circumferentially elastic fabric having a limited vertical stretch. The fold line defines the top 102 of the insert and provides a smooth non-irritating, non-rolling edge. The fabric has alternating courses of jersey knit stitches of non-elastomeric yarns of stretch nylon, and a covered elastomeric yarn is inlaid into every other course of the jersey stitches.

Other embodiments will be within the scope of the following claims.

What is claimed is:

1. In a full length therapeutic stocking of the type including a boot portion including elastomeric yarn, waist support means spaced above the boot portion, and a hip panel extending between the boot portion and the waist support means, that improvement including a pair of stocking supports extending between and attached to said waist support means and said boot portion, each of said supports comprising a strip of fabric extending from a respective point at said waist support means to and terminating at a respective point at the upper edge of said boot portion, and each of said respective points of one of said supports being spaced circumferentially of said stocking from the corresponding respective point of the other of the supports.

2. The stocking of claim 1 wherein the distance between said points at said upper edge of said boot portion is in the range of 20% to 40% the circumference of the upper edge of said boot portion.

3. The stocking of claim 1 wherein said boot portion includes an insert of circumferentially elastic fabric extending downwardly from said upper edge of said boot portion and positioned intermediate said respective points at said upper edge.

4. The stocking of claim 3 wherein said insert is of double fabric and the fold line thereof defines a portion of said upper edge of said boot portion.

5. The stocking of claim 3 wherein said insert is in the general shape of a rounded "V" and a portion of said boot portion is slit to permit incorporation of said insert.

6. The stocking of claim 1 wherein said points are equidistant from the center of said hip panel.

7. In a full length therapeutic stocking of the type including a boot portion including elastomeric yarn, waist support means spaced above the boot portion, and a hip panel extending between the boot portion and the waist support means, that improvement wherein said hip panel defines a pair of inner edges each extending from a respective point at said waist support means to and terminating at a respective point at the upper edge of said boot portion, an inelastic edging is stitched to and overlies each of said inner edges, and each of said respective points of one of said edges being spaced circumferentially of said stocking from the corresponding respective point of the other of said edges.

8. The stocking of claim 7 wherein the distance between said points at the upper edge of said boot portion is in the range of 20% to 40% of the circumference of the upper edge of said boot portion.

9. The stocking of claim 7 wherein said boot portion includes an insert of circumferentially elastic fabric extending downwardly in the general shape of a rounded "V" from the upper edge of said boot portion and positioned intermediate said respective points at said upper edge.

10. In a full length therapeutic stocking of the type including a boot portion including elastomeric yarn, waist support means spaced above the boot portion, and a hip panel extending between the boot portion and the waist support means, that improvement including a pair of stocking supports extending between and attached to said waist support means and said boot portion, each of said supports comprising an inelastic edging stitched to and overlying a respective inner edge of said hip panel and extending from a respective point at said waist support means to a respective point at the upper edge of said boot portion, and each of said respective points of one of said supports being spaced circumferentially of said stocking from the corresponding respective point of the other of the supports.

* * * * *

UNITED STATES PATENT AND TRADEMARK OFFICE
CERTIFICATE OF CORRECTION

PATENT NO. : 4,180,869
DATED : January 1, 1980
INVENTOR(S) : John E. Pendergrass and Cynthia A. Wichman It is certified that error appears in the above–identified patent and that said Letters Patent are hereby corrected as shown below:

Inventor "John E. Pedergrass" should be --John E. Pendergrass--

Signed and Sealed this

Fifth Day of August 1980

[SEAL]

Attest:

SIDNEY A. DIAMOND

Attesting Officer

Commissioner of Patents and Trademarks